United States Patent [19]
Wurtman et al.

[11] Patent Number: 5,206,218
[45] Date of Patent: Apr. 27, 1993

[54] REDUCING POST-PRANDIAL FLUCTUATIONS IN PLASMA CONCENTRATIONS OF LARGE NEUTRAL AMINO ACIDS (LNAA)

[75] Inventors: Richard J. Wurtman; Judith J. Wurtman, both of Boston, Mass.

[73] Assignee: Interneuron Pharmaceuticals, Inc., Lexington, Mass.

[21] Appl. No.: 332,871

[22] Filed: Apr. 3, 1989

[51] Int. Cl.$^5$ .......................... C07D 37/02; A23J 3/04; A23J 3/08
[52] U.S. Cl. .......................................... 514/2; 514/12; 514/21; 548/496
[58] Field of Search ................................ 514/2, 12, 21

[56] References Cited

PUBLICATIONS

Fernstrom J. D. and Wurtman R. J. "Brain Serotonin Content: Physiological Regulation by Plasma Neutral Amino Acids." *Science* 178: 414–416 (1972).
Fernstrom J. D. and Faller D. V. "Neutral Amino Acids in the Brain: Changes in Response to Food Ingestion." *Journal of Neurochemistry* 30: 1531–8 (1978).
Yokogoshi H. and Wurtman R. J. "Meal Composition and Plasma Amino Acid Ratios: Effect of Various Proteins or Carbohydrates, and of Various Protein Concentrations." *Metabolism* 35/9: 837–842 (1986).
Juncos J. L., Fabbrini G., Mouradian M. M., Serrati C, and Chase T. N. "Dietary Influences on the Antiparkinsonian Response to Levodopa." *Arch Neurol* 44: 1003–5 (1987).
N. G. Gillespie et al., *J. Am. Dietetic Assoc.*, 62(S): 525–528 (1973).
D. Markovitz et al., *Proc. Fed. Am. Soc. Exp. Biol.* 36(3): Abstr. 609 (1977).
Fernstrom et al., *Amer. J. Clin. Nutrition*, 32: 1912–1922 (1979).
Markovitz and Fernstrom, *Science*, 179: 1014–1015 (1977).
Cotzias et al., *Adv. in Neurol.*, 2: 265–277 (1973).
Wurtman and Caballero, *New Eng. J. Med.*, 319: 1288–1289 (1988).

*Primary Examiner*—David B. Springer
*Attorney, Agent, or Firm*—Pennie & Edmonds

[57] ABSTRACT

Methods of reducing post-prandial fluctuations in plasma levels of large, neutral amino acids (LNAA), as well as compositions useful in that method. The foods and compositions comprise a carbohydrate to protein ratio of from about 3:1 to about 6:1 and, in a specific embodiment, a ratio of 4:1, which results in minimizing the variability in responses individuals exhibit to drugs which are LNAA.

8 Claims, 2 Drawing Sheets

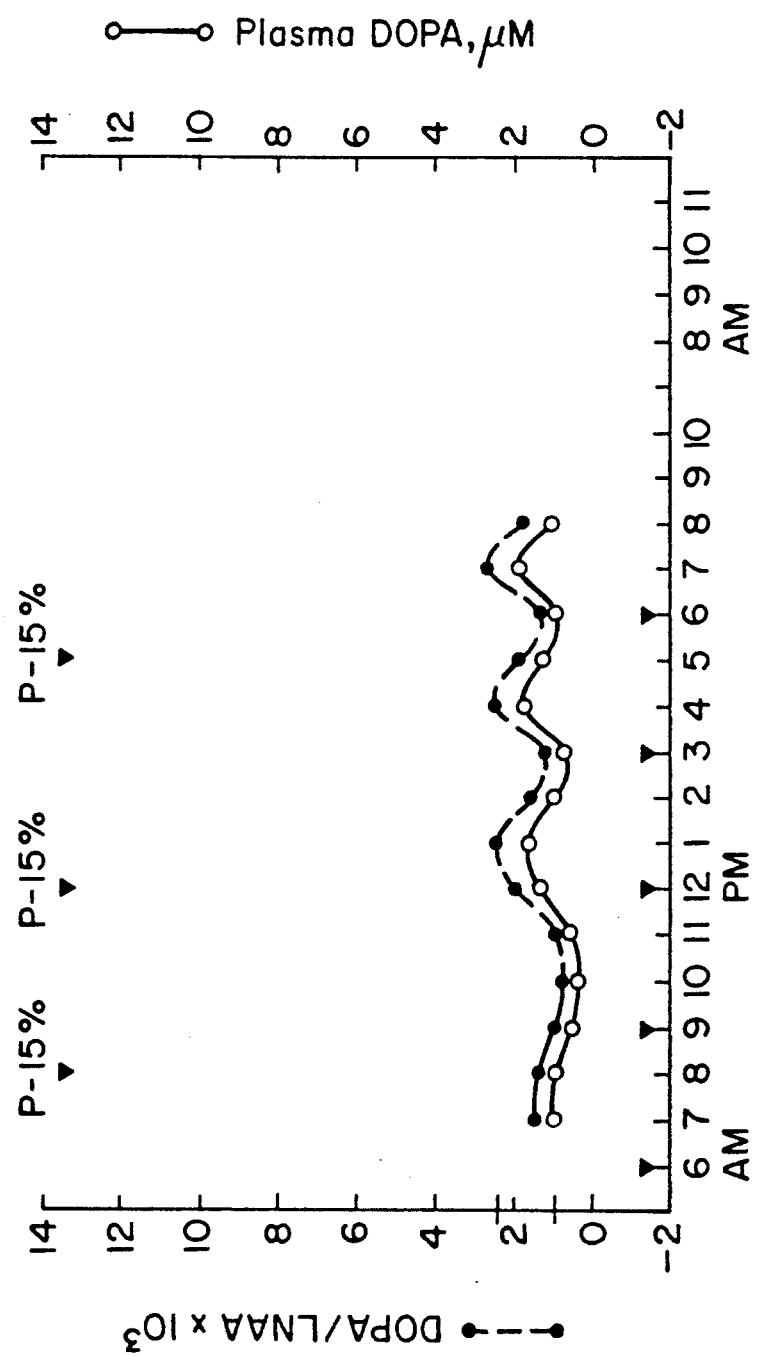

REDUCING POST-PRANDIAL FLUCTUATIONS IN PLASMA CONCENTRATIONS OF LARGE NEUTRAL AMINO ACIDS (LNAA)

BACKGROUND

Treatment of some diseases, such as Parkinson's Disease, includes administration of a drug which is a large neutral amino acid (LNAA) and which must cross the blood-brain barrier to be effective. For example, L-dopa, alphamethyldopa (Aldomet) and 5-hydroxytryptophan, which are LNAA, can be administered in the treatment of Parkinson's Disease, hypertension or myoclonus. Patients who take such drugs may exhibit variability in their responses to them and may suffer adverse effects, such as L-Dopa induced dyskinesia, from them.

It would be useful to have a means by which an individual's response to such drugs can be controlled and the adverse effects reduced.

SUMMARY OF THE INVENTION

The present invention pertains to a method of reducing post-prandial fluctuations in plasma LNAA levels in an individual, particularly for the purpose of reducing variability in the individual's response to treatment with drugs which are themselves LNAA. It further relates to compositions for administration to an individual to reduce fluctuations in plasma concentrations of large neutral amino acids (LNAA). As used herein, LNAA includes amino acids which have a single amino group and a single carboxyl group, for example, leucine, isoleucine, tyrosine, valine, phenylalanine and tryptophan.

The present composition comprises an appropriate ratio of carbohydrates to protein to reduce fluctuations in plasma LNAA levels, when administered to an individual. Most commonly, the ratio of carbohydrate to protein in the composition is about 4:1. However, the ratio of carbohydrate to protein used can vary from about 3:1 to about 6:1, depending on the individual to whom such a composition is administered. Such characteristics as body weight and plasma amino acid responses will be considered in determining an appropriate carbohydrate to protein ratio for an individual. The present invention also relates to methods of administering foods or compositions which minimize post-prandial fluctuations in plasma LNAA levels. Administration of such compositions or of foods selected to contain a carbohydrate to protein ratio of from about 3:1 to about 6:1 is particularly valuable in minimizing the variability in responses some individuals exhibit to drugs, such as L-dopa, which are themselves LNAA. If an individual wishes to minimize fluctuations in plasma LNAA for only a segment of the twenty-four hour day, the present method can be used to determine the composition of meals and/or snacks consumed during that segment.

For example, foods which provide about 120-500 grams of carbohydrate per day and 40-100 grams of protein per day can be administered to an individual suffering from Parkinson's disease who is being treated with L-dopa and whose response to the drug varies and may be associated with adverse effects, such as dyskinesia.

BRIEF DESCRIPTION OF THE DRUG

The figure is a graphic representation of the effects of administration of meals in which the ratio (per meal) of carbohydrate to protein was about 4:1 to an individual with Parkinson's Disease who was taking L-dopa. Times at which meals were consumed are indicated by Δ.

FIG. 1 is a graphic representation of L-dopa toxicity, as represented by dyskinesis, the extent to which its administration was associated with dyskinesis at hourly intervals.

FIG. 2 is a graphic representation of plasma branched-chain amino acid (BCAA) levels (e.g., isoleucine, leucine or valine) at hourly intervals in the individual. The branched chain amino acids are the most abundant LNAA in the plasma and their levels are most affected by eating carbohydrates or proteins; thus, they are the main determinant of uptake of LNAA drugs into the brain. The ability of the new diet to minimize variations in plasma BCAA level paralleled its damping effects on variations in plasma LNAA.

FIG. 3 is a graphic representation of plasma DOPA levels (o—o) and of the plasma DOPA/LNAA ratio (●—●) at hourly intervals in the individual.

DETAILED DESCRIPTION OF THE INVENTION

Figures 1, 2:
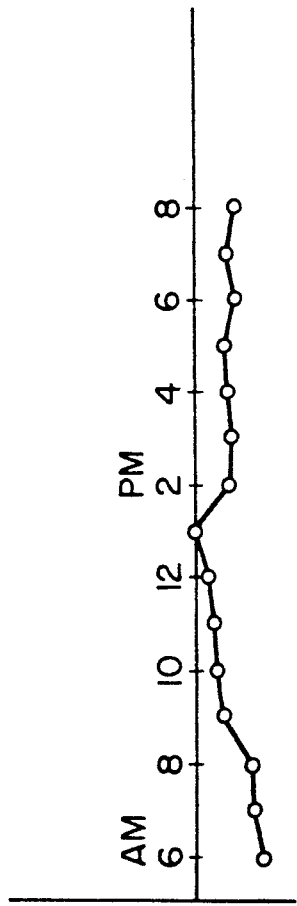

The present invention is based on the discovery that fluctuations in plasma LNAA levels, particularly post-prandial fluctuations, can be reduced or controlled and, as a result, that the variability in response in an individual to administration of a drug or drugs which is/are LNAA can also be reduced or controlled. The ability to reduce plasma LNAA level fluctuation and, concomitantly, variation in response to a drug which is a LNAA is of particular value in the management of individuals, such as those with Parkinson's disease, who take such a drug or drugs for treatment of a disease or other condition. It is now possible to improve treatment of individuals taking LNAA because the adverse effects can be ameliorated or eliminated and, as a result, individuals are able to continue to follow their prescribed treatment.

It is known that post-prandial plasma levels of LNAA can vary widely and that such levels are affected by the carbohydrate and protein content of foods consumed.

Fernstrom et al. report that plasma leucine was 60 nmoles/ml after a protein-free, high carbohydrate breakfast, and about 240 nmoles/ml after a high protein breakfast. Plasma valine varied from about 100 nmol/ml to 50 nmols/ml under these conditions, and plasma isoleucine ranged from 30 to 60 nmols/ml. *Am. J. Clin. Nutr.*, 32:1912–1922 (1979). A meal rich in carbohydrates elicits the secretion of insulin and facilitates the passage of LNAA out of the blood stream and into peripheral tissues, thus reducing circulating levels. In contrast, a meal rich in protein tends to increase blood levels of LNAA. Some of the LNAA in the protein passes right through the liver, without being metabolized, and into the systemic circulation.

These fluctuations normally are important determinants of brain levels of one of the LNAA, tryptophan, and thus of the formation of the neurotransmitter serotonin from tryptophan. This is due to the fact that all of the LNAA in the plasma must compete for access to a common transport system in order to be transported across the blood-brain barrier. Therefore, a high-protein meal will tend to diminish brain tryptophan because it causes blood levels of the other LNAA to increase more, proportionately, than those of tryptophan. In contrast, a high-carbohydrate meal will tend to increase brain tryptophan and serotonin levels because insulin secreted in response to the carbohydrates lowers the other LNAA.

Post-prandial changes in plasma LNAA are also important determinants of brain levels of drugs which are themselves LNAA and must compete with other LNAA for transport across the blood-brain barrier. There are a number of diseases which are treated with drugs, such as L-dopa, that compete with circulating large neutral amino acids (LNAA) for passage from the blood stream into the brain. L-dopa and such other drugs as alphamethyldopa (Aldomet) and 5-hydroxy-tryptophan which are themselves LNAA, must enter the brain in order to be effective. Brain levels of one such drug, L-dopa, are known to vary with the plasma dopa ratio (i.e., the ratio of the plasma dopa concentration to the summed concentrations of the other LNAA) and not with the dopa concentration alone. See Markovitz et al., *Science*, 197:1014–1015 (1977). Patients who take such drugs may exhibit variability in response to them, as well as adverse effects, such as dyskinesia.

It has now been shown that these post-prandial fluctuations in the plasma LNAA can be controlled or reduced and, as a result, that variability in the clinical responses to treatment with drugs which are LNAA can also be reduced or eliminated.

The present invention relates to a method for reducing fluctuations in plasma levels of large neutral amino acid and to compositions and combinations of foods having a selected carbohydrate to protein ratio for use in treating individuals who exhibit variability in responses to drugs, such as L-dopa, which are themselves LNAA, and which must enter the brain in order to be effective. The term LNAA, as used herein, includes amino acids which comprise a single amino and a single carboxyl group such as leucine, isoleucine, valine, tyrosine, phenylalanine, and tryptophan. Use of the method of the present invention with an individual who is taking a drug (or drugs) which is a LNAA makes it possible to reduce the fluctuations in post-prandial plasma levels of LNAA. (That is, it makes it possible to control the post-prandial LNAA levels in such a manner that they exhibit less variation than is evident when the individual being treated consumes his or her "usual" diet.

In one embodiment of the present invention, a composition in which the carbohydrate to protein ratio is approximately 4:1 is administered to an individual. Depending on the individual, the ratio of carbohydrate to protein can vary from about 3:1 to about 6:1. For example, for individuals with reduced insulin sensitivity (i.e., secondary to type II diabetes, obesity, or elevated lean body mass), it may be necessary to provide a larger total amount or higher proportion of dietary carbohydrate, in order to balance the protein-induced rise in plasma LNAA, or to reduce the percent of dietary protein.

In another embodiment, foods for meals or snacks can be prepared which provide an effective carbohydrate to protein ratio to minimize post-prandial fluctuations in plasma concentrations of LNAA. Foods which provide approximately 120–500 grams of carbohydrate per day or 87–116 grams of carbohydrate per meal and approximately 40–100 grams of protein per day or 20–27 grams of protein per meal can be administered to an individual. For example, approximately 250 grams of carbohydrate per day and approximately 70 grams of protein per day will minimize fluctuations in plasma LNAA levels. The actual quantity (or range of quantities) of carbohydrate and of protein to be administered to an individual will be determined empirically, by determining the proportion that elicits the optimal clinical response (i.e., greatest drug response and fewest side effects). If necessary, the optimal amounts of carbohydrates and protein can be affirmed by testing their effects on plasma LNAA levels and ratios. As described in the Exemplification, for practical purposes, LNAA measured are leucine, isoleucine, valine, tyrosine, phenylalanine and tryptophan. The post-prandial changes are measured between 1 and 5 hours after the meal or snack has been consumed. Assessment of values obtained in this manner make it possible to determine an appropriate carbohydrate to protein ratio for an individual (i.e., one effective in reducing or eliminating fluctuations in plasma LNAA levels and, concomitantly, in reducing or eliminating variable responses to a drug, such as L-dopa, which is a LNAA). For purposes of calculation, the carbohydrates in the foods may be normalized in terms of their ability to trigger insulin release (foods with a high glycenic index include among others potato, starch or sucrose.

According to the method of the present invention, compositions or foods comprising an effective carbohydrate to protein ratio can be administered to individuals to minimize the variability in clinical responses to treatment with drugs which are LNAA. For example, drugs such as L-dopa (levodopa), Aldomet (alphamethyldopa), and 5-hydroxytryptophan are LNAA and must compete with other LNAA for transport across the blood-brain barrier.

The present invention will now be illustrated by the following Exemplification, which is not intended to be limiting in any way.

EXEMPLIFICATION

Assessment of post-prandial plasma levels of LNAA and dopa

The subject was an otherwise healthy 59-year old with a 12-year history of Parkinson's Disease, which was poorly controlled on Sinimet (i.e., L-dopa and a peripheral decarboxylase inhibitor) plus a dopamine agonist. The subject had experienced difficulty in controlling the marked fluctuations in his symptoms. At one time of day he might be vastly overmedicated, and suffer from very disturbing abnormal movements, or dyskinesis; at another time, not too much later, he would be undermedicated, and suffer from rigidity and tremor. To study plasma levels of dopa and LNAA along with the clinical responses to L-dopa, the subject consumed test meals designed to minimize post-prandial fluctuations in plasma LNAA levels.

The subject consumed three meals, each which contained a carbohydrate to protein ratio of approximately 4:1 (87–116 grams of carbohydrate and 20–27 grams of protein for breakfast, lunch and dinner).

Under these conditions, the patient did not exhibit symptoms of dopa toxicity (i.e., dyskinesias) (Panel A of the Figure). Dyskinesis had previously been a problem for this individual. Plasma samples were obtained at hourly intervals and assayed for dopa and LNAA. Post-prandial LNAA levels of leucine, isoleucine and valine varied by only ±15%. The plasma dopa ratio also varied by less than ±20% throughout the day. (Panel C of the Figure).

Furthermore, additional work showed that when the subject consumed a meal rich in carbohydrate, but lacking protein, he exhibited severe dyskinesis. In contrast, when the subject consumed a high-protein meal, he exhibited signs of undermedication.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. A composition for administration to an individual to reduce fluctuations in plasma large neutral amino acid (LNAA) levels, comprising a ratio of carbohydrate to protein of approximately 3:1 to approximately 6:1.

2. A composition as in claim 1 wherein the LNAA are selected from the group consisting of: leucine, isoleucine, valine, tryosine, phenylalanine, and tryptophan.

3. A method of reducing post-prandial fluctuations in plasma concentrations of LNAA, comprising administering to an individual an effective quantity of a composition comprising a ratio of carbohydrate to protein of from approximately 3:1 to approximately 6:1.

4. A method as in claim 3 wherein the LNAA are selected from the group consisting of: leucine, isoleucine, valine, tyrosine, phenylalanine, and tryptophan.

5. A method of reducing post-prandial fluctuations in plasma concentrations of LNAA, comprising administering to an individual foods which provide a ratio of carbohydrate to protein of from approximately 3:1 to approximately 6:1.

6. A method as in claim 5 wherein the LNAA are selected from the group consisting of: leucine, isoleucine, valine, tyrosine, phenylalanine, and tryptophan.

7. A method of reducing post-prandial fluctuations in plasma concentration of LNAA comprising administering to an individual foods which provide approximately 20–27 grams of protein per meal or approximately 5–6 grams of protein per snack and approximately 87–116 grams of carbohydrate per meal or approximately 25–29 grams of carbohydrate per snack.

8. A method as in claim 7 wherein the LNAA are selected from the group consisting of: leucine, isoleucine, valine, tyrosine, phenylalanine, and tryptophan.

* * * * *